(12) United States Patent
Franc et al.

(10) Patent No.: US 11,389,553 B2
(45) Date of Patent: Jul. 19, 2022

(54) DECONTAMINATION DEVICE AND METHOD

(71) Applicant: CLARANOR, Montfavet (FR)

(72) Inventors: Janyce Franc, Avignon (FR); Christophe Riedel, Avignon (FR)

(73) Assignee: CLARANOR, Montfavet (FR)

( * ) Notice: Subject to any disclaimer, the term of this patent is extended or adjusted under 35 U.S.C. 154(b) by 433 days.

(21) Appl. No.: 16/347,756

(22) PCT Filed: Nov. 7, 2017

(86) PCT No.: PCT/EP2017/078478
§ 371 (c)(1),
(2) Date: May 29, 2019

(87) PCT Pub. No.: WO2018/083340
PCT Pub. Date: May 11, 2018

(65) Prior Publication Data
US 2019/0282717 A1    Sep. 19, 2019

(30) Foreign Application Priority Data
Nov. 7, 2016 (FR) ...................... 1660741

(51) Int. Cl.
*B29C 49/06* (2006.01)
*A61L 2/10* (2006.01)
(Continued)

(52) U.S. Cl.
CPC ................. *A61L 2/10* (2013.01); *A61L 2/085* (2013.01); *B29C 49/06* (2013.01); *B67B 3/003* (2013.01);
(Continued)

(58) Field of Classification Search
CPC ........ A61L 2/10; A61L 2/085; A61L 2202/23; A61L 2202/11; B67B 3/003; B29C 49/06;
(Continued)

(56) References Cited

U.S. PATENT DOCUMENTS 4,473,530 A * 9/1984 Villa-Real .......... G01N 21/8483
                                                                  215/6
6,037,598 A    3/2000 Cicha
(Continued)

FOREIGN PATENT DOCUMENTS

CN    105492185 A    4/2016
CN    105658406 A    6/2016
(Continued)

OTHER PUBLICATIONS

French Search Report from French Patent Application No. 1660741, dated Jul. 6, 2017.
(Continued)

*Primary Examiner* — Monica A Huson
(74) *Attorney, Agent, or Firm* — Greer, Burns & Crain, Ltd

(57) ABSTRACT

A method for decontaminating a tube of which a first open end forms an inner neck towards the inside of the tube and an outer neck towards the outside of the tube, the method including:
  initially raising the temperature of the tube, then
  subjecting the tube to ultraviolet radiation, that includes emitting ultraviolet radiation by radiation emission apparatus, and subjecting the inside of the tube, the outer neck and the inner neck to the ultraviolet radiation, in which the first end is inserted into a cavity arranged to reflect the ultraviolet radiation emitted by the emission apparatus and to direct this ultraviolet
(Continued)

radiation into the tube through the first end, onto the outer neck of the tube and onto the inner neck of the tube.

15 Claims, 3 Drawing Sheets

(51) Int. Cl.
| | |
|---|---|
| *A61L 2/08* | (2006.01) |
| *B67B 3/00* | (2006.01) |
| *B29B 13/08* | (2006.01) |
| *B29C 49/42* | (2006.01) |
| *B29C 49/46* | (2006.01) |
| *B29K 667/00* | (2006.01) |
| *B67C 3/26* | (2006.01) |
| *B67C 3/22* | (2006.01) |

(52) U.S. Cl.
CPC ........ *A61L 2202/11* (2013.01); *A61L 2202/23* (2013.01); *B29B 13/08* (2013.01); *B29C 49/4252* (2013.01); *B29C 49/4268* (2013.01); *B29C 2049/4673* (2013.01); *B29K 2667/003* (2013.01); *B67C 2003/227* (2013.01); *B67C 2003/2688* (2013.01)

(58) Field of Classification Search
CPC ........ B29C 49/4252; B29C 2049/4673; B29C 49/4268; B67C 2003/227; B67C 2003/2688; B29B 13/08; B29K 2667/003
See application file for complete search history.

(56) References Cited

U.S. PATENT DOCUMENTS

| | | |
|---|---|---|
| 8,083,512 B2 | 12/2011 | Adriansens |
| 9,889,217 B2 | 2/2018 | Franc et al. |
| 2002/0146343 A1* | 10/2002 | Jenkins .................... A61L 2/24 |
| | | 422/24 |
| 2012/0273693 A1 | 11/2012 | Houde |
| 2014/0265039 A1 | 9/2014 | Bellec et al. |
| 2016/0193775 A1 | 7/2016 | Lewin et al. |
| 2016/0193776 A1 | 7/2016 | Lewin et al. |

FOREIGN PATENT DOCUMENTS

| | | |
|---|---|---|
| EP | 1918208 A1 | 5/2008 |
| EP | 2138298 A2 | 12/2009 |
| EP | 2805912 A1 | 11/2014 |
| EP | 2961437 B1 | 10/2016 |
| JP | 11263322 A | 9/1999 |

OTHER PUBLICATIONS

International Search Report from International Patent Application No. PCT/EP2017/078478, dated Jan. 29, 2018.

* cited by examiner

DECONTAMINATION DEVICE AND METHOD

BACKGROUND

The present invention relates to a decontamination device and method.

Such a device allows a user to decontaminate an object such as for example a plastic preform on a production line for manufacture and filling of a plastic bottle or container. The field of the invention is more particularly that of microbiological decontamination.

Methods are known for decontaminating a preform.

Document US2014/0265039 describes a method in which means for emitting ultraviolet radiation are introduced inside the preform in order to decontaminate it.

The use of ultraviolet inside the preform, i.e. as close as possible to the greatest surface to be decontaminated, allows a satisfactory level of decontamination but has the drawbacks of:

slowing the rate of decontamination, and/or having a very bulky device comprising numerous stations with UV lamps so as to ensure production-line speeds, and/or risking breaking elements inside the preform and leaving debris therein, and/or failing to decontaminate the outer part of the neck of the preform.

The aim of the present invention is to resolve at least one of these drawbacks while continuing to provide a satisfactory level of decontamination of the inner surface of the preform, compatible for example with the agri-food industry, in particular with "ultra-clean" production lines having an intermediate asepsis level.

SUMMARY

This aim is achieved with a method for decontaminating a tube a first open end of which forms an inner neck towards the inside of the tube and an outer neck towards the outside of the tube, said method comprising:

initially raising the temperature of the tube, then subjecting the tube to ultraviolet radiation, comprising emitting ultraviolet radiation by radiation emission means, and subjecting the inside of the tube, the outer neck and the inner neck to the ultraviolet radiation, preferably when the first end is introduced inside a cavity arranged in order to reflect the ultraviolet radiation emitted by the emission means and to direct this ultraviolet radiation to the inside of the tube through the first end, onto the outer neck of the tube and onto the inner neck of the tube.

The tube can comprise:

a second end forming a base of the tube, and a body extending between the first end and the second end.

When the tube is subjected to the ultraviolet radiation, the second end of the tube may not be located in the cavity.

When the tube is subjected to the ultraviolet radiation, the body of the tube may not be located in the cavity.

All the parts of the tube (or all the parts of the tube except for the neck) are preferably at a temperature above or equal to 85° C. when the tube is subjected to the ultraviolet radiation.

When the tube is subjected to the ultraviolet radiation, the radiation emission means may not be inserted inside the tube.

The method according to the invention preferably does not comprise any insertion inside the tube of any other radiation emission means.

The ultraviolet radiation is preferably pulsed ultraviolet light having:

a pulse duration less than 500 μs, and/or a luminous energy per pulse of at least 70 joules, and/or a pulse frequency of at least 0.5 Hz, or more generally, a pulse frequency controlled as a function of the rate of advance of the tubes to be decontaminated.

The tube can be a tube made from plastic material.

The method according to the invention can comprise at least one of the following steps after subjecting the tube to the ultraviolet radiation, preferably in the following order:

modifying the tube shape, and/or filling the tube, and/or fixing a cap on the tube in contact with the outer neck.

The method according to the invention may not comprise raising the temperature of the tube:

between subjecting the tube to the ultraviolet radiation and modifying the shape of the tube, and/or between subjecting the tube to the ultraviolet radiation and filling the tube, and/or between subjecting the tube to the ultraviolet radiation and fixing the cap.

The method according to the invention can comprise subjecting the cap to ultraviolet radiation before it is fixed on the tube.

The method according to the invention can comprise no chemical decontamination of the tube.

The initial temperature increase can be obtained by passing the tube through an oven and/or by subjecting the tube to an infrared lamp.

The initial temperature increase preferably raises all parts of the tube to a temperature above or equal to 90° C.

According to yet another aspect of the invention, a device for decontaminating a tube is proposed, comprising:

means for moving, along a decontamination path in a direction of travel, a tube a first open end of which forms an inner neck towards the inside of the tube and an outer neck towards the outside of the tube, initial heating means, arranged in order to raise the temperature of the tube on the decontamination path, means for subjecting the tube to ultraviolet radiation, situated on the decontamination path downstream of the heating means with respect to the direction of travel, comprising means for subjecting the inside of the tube, the outer neck and the inner neck to the ultraviolet radiation.

The means for subjecting the tube to ultraviolet radiation preferably comprise emission means arranged in order to emit the ultraviolet radiation.

The means for subjecting the tube to ultraviolet radiation preferably comprise a cavity situated on the decontamination path downstream of the heating means with respect to the direction of travel, the movement means and the cavity being arranged together so that the first end is introduced inside the cavity when the tube arrives at the cavity, the cavity being arranged in order to reflect the ultraviolet radiation emitted by the emission means and in order to direct this ultraviolet radiation to the inside of the tube through the first end, onto the outer neck of the tube and onto the inner neck of the tube so as to subject the inside of the tube, the outer neck and the inner neck to the ultraviolet radiation when the tube arrives at the cavity.

The tube can comprise:
a second end forming a base of the tube, and
a body extending between the first end and the second end
and the movement means and the cavity can be arranged together so that the second end of the tube is not located in the cavity when the tube arrives at the cavity.

The movement means and the cavity can be arranged together so that the body of the tube is not located in the cavity when the tube arrives at the cavity.

The heating means, the cavity and the movement means linking the heating means to the cavity can be arranged so that all the parts of the tube are at a temperature above or equal to 85° C. when the tube arrives at the cavity.

The radiation emission means may not be arranged in order to be inserted inside the tube when the tube arrives at the cavity.

The device according to the invention may not comprise any other radiation emission means arranged in order to be inserted inside the tube when the tube arrives at the cavity.

The emission means can be arranged in order to emit the ultraviolet radiation in the form of pulsed ultraviolet light having:
a pulse duration less than 500 µs, and/or
a luminous energy per pulse of at least 70 joules, and/or
a pulse frequency of at least 0.5 Hz, or more generally, a pulse frequency controlled as a function of the rate of advance of the tubes to be decontaminated.

The device according to the invention can comprise at least one of the following means situated on the decontamination path downstream of the cavity with respect to the direction of travel, preferably in the following order with respect to the direction of travel:
means for modifying the shape of the tube, and/or
means for filling the tube, and/or
fixing means arranged for fixing a cap on the tube in contact with the outer neck of the tube.

The device according to the invention may not comprise means for raising the temperature of the tube:
along the decontamination path between the cavity and the means for modifying the shape of the tube, and/or
along the decontamination path between the cavity and the means for filling the tube, and/or
along the decontamination path between the cavity and the means for fixing the cap.

The device according to the invention can comprise means for subjecting the cap to ultraviolet radiation before it is fixed on the tube by the fixing means.

The device according to the invention can comprise no means for chemical decontamination of the tube.

The heating means can comprise an oven and/or an infrared lamp.

The heating means can be arranged in order to raise all the parts of the tube to a temperature above or equal to 90° C.

BRIEF DESCRIPTION OF THE DRAWINGS

Other advantages and features of the invention will become apparent on reading the detailed description of implementations and embodiments which are in no way limitative, and from the following attached drawings, in which.

DETAILED DESCRIPTION

As these embodiments are in no way limitative, variants of the invention can be considered comprising only a selection of the characteristics described or illustrated hereinafter, in isolation from the other characteristics described or illustrated (even if this selection is isolated within a phrase containing other characteristics), if this selection of characteristics is sufficient to confer a technical advantage or to differentiate the invention with respect to the state of the prior art. This selection comprises at least one, preferably functional, characteristic without structural details, and/or with only a part of the structural details if this part alone is sufficient to confer a technical advantage or to differentiate the invention with respect to the state of the prior art.

Figure 1:
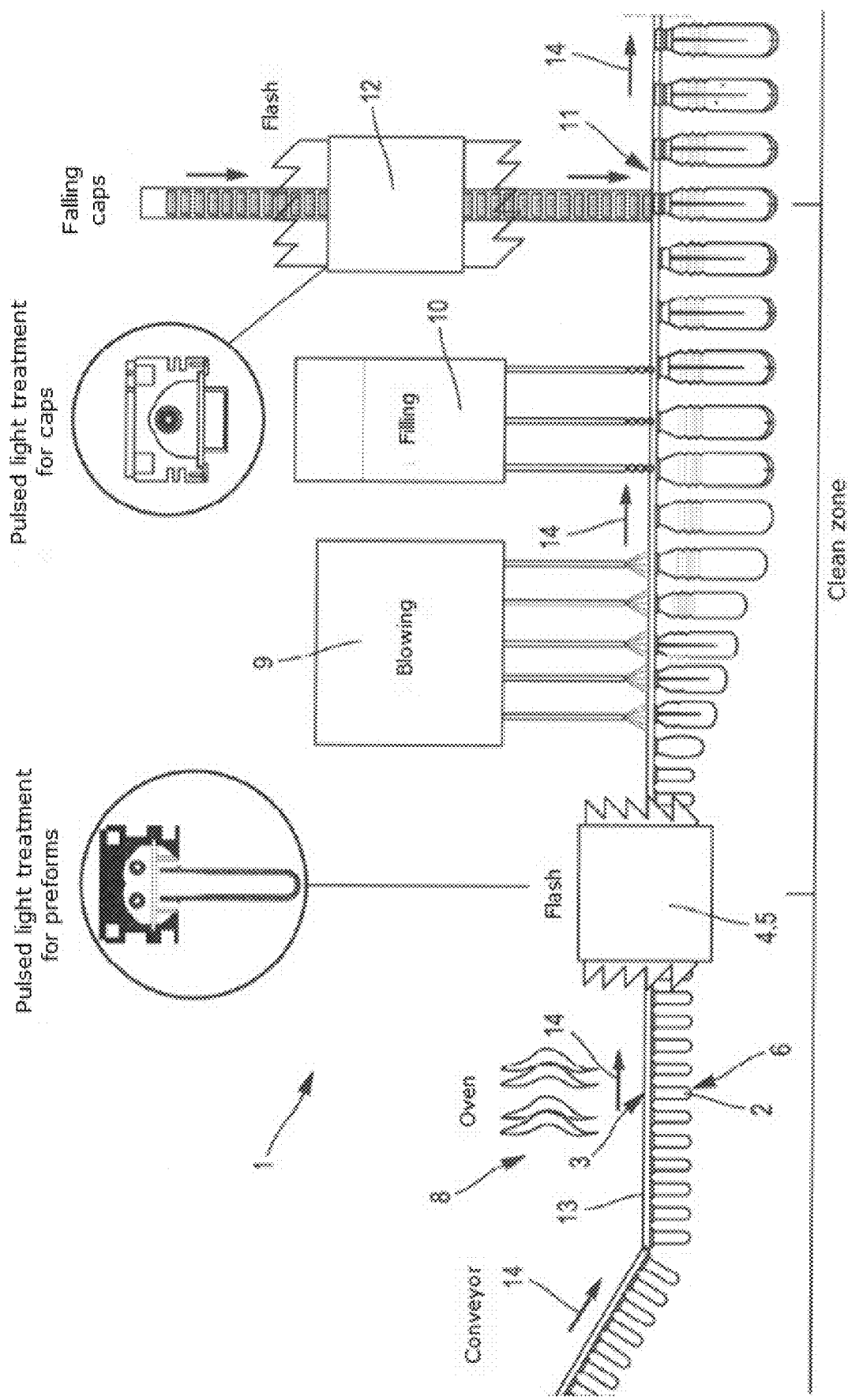
FIG. 1 is a diagrammatic view of an embodiment of the device 1 according to the invention implementing an embodiment of a method according to the invention, which are preferred embodiments of the invention.
Figure 2:
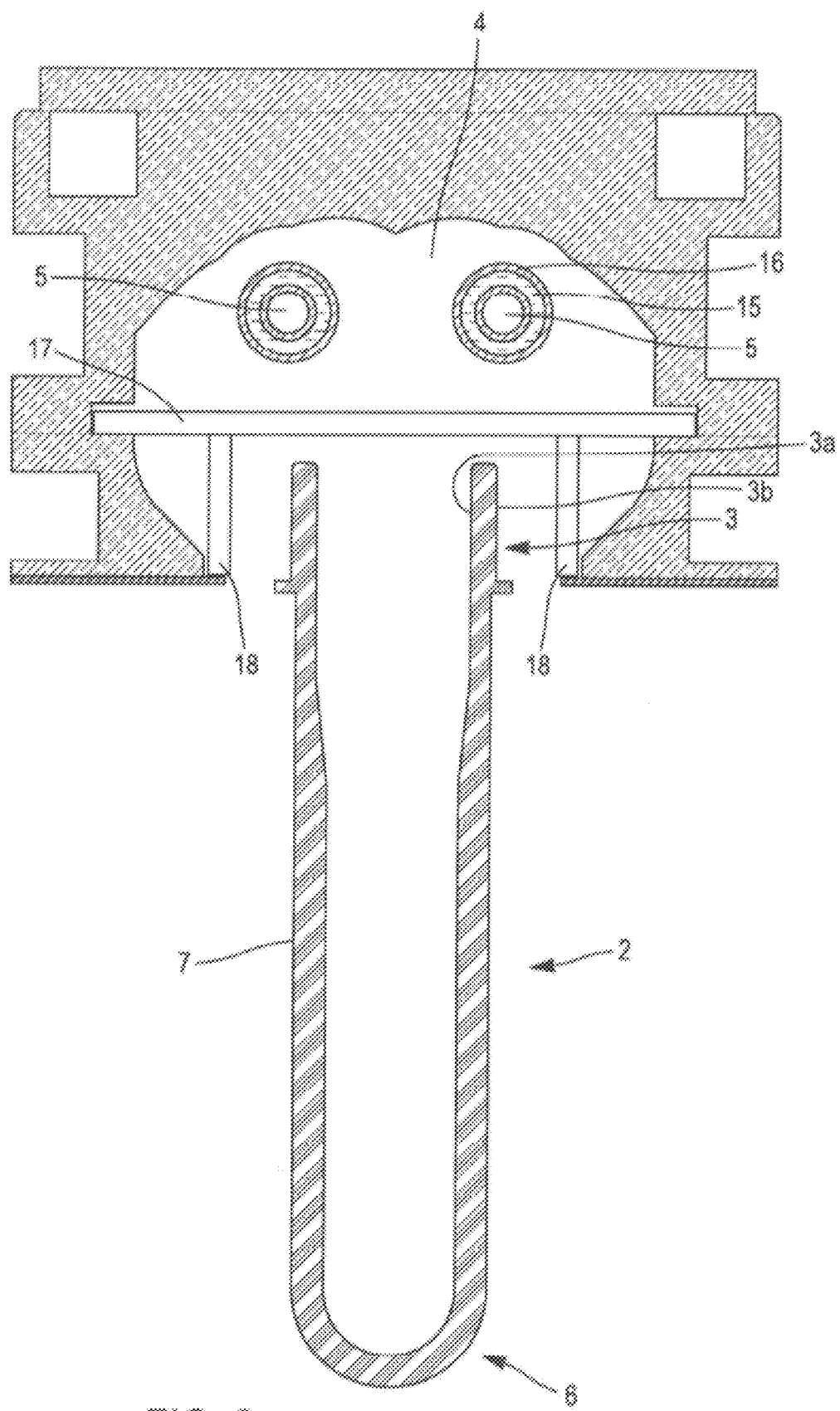
FIG. 2 is a diagrammatic profile view of the position of a tube 2 inserted inside a cavity 4 of the device 1 in FIG. 1.

Firstly, with reference to FIGS. 1 to 3, an embodiment of the device according to the invention will be described, implementing an embodiment of a method according to the invention.

The device 1 for microbiological decontamination of a tube 2 comprises means 13 for moving a tube 2 along a decontamination path in a direction of travel 14.

These movement means comprise for example a conveyor bearing the tube 2, for example:
of the stainless steel moving track type, and/or
of the "gripper" type. In this case, the transport of the preforms between the oven and the blower is typically carried out by grippers, which catch the preforms below the neck. In fact, in the oven, a mandrel holds the preform by the inside of the bottle neck, and makes the preform turn on itself at the same time as it is moved opposite the infrared arrays. The preform cannot be held by its inside. Before the mandrel releases the preform, it is taken by a gripper which is mounted on a carousel and which captures the preform, separates it from the previous one (in the oven the preforms are spaced apart by 35 mm, and in the blower by approximately 400 mm, due to the space requirement of the moulds), by acceleration, before the preform is taken by the mould which is also mounted on a carousel.

The tube 2 comprises:
a first open end 3 which forms an inner neck 3a towards the inside of the tube 2 and an outer neck 3b towards the outside of the tube 2,
a second closed end 6 forming a base of the tube 2, and
a body 7 extending between the first end 3 and the second end 6.

The device 1 comprises initial heating means 8, arranged in order to raise the temperature of the tube 2 on the decontamination path.

The heating means 8 comprise an oven, more precisely an infrared halogen lamp oven of 1000 watts or even several tens of kilowatts for a higher output.

The heating means 8 are arranged in order to raise all the parts of the tube 2 to a temperature above or equal to 90° C., preferably above or equal to 100° C., preferably above or equal to 115° C., preferably above or equal to 142° C.

The device 1 comprises means for subjecting the tube 2 to ultraviolet radiation, more precisely for subjecting:
the inner neck 3a of the tube 2,
the outer neck 3b of the tube 2, and the inside of the tube 2, more precisely:
  the inner neck 3a already mentioned
  the body 7 of the tube on the inner side of the tube 2
  the base 6 of the tube 2 on the inner side of the tube 2 to ultraviolet radiation.

These means for subjecting the tube 2 to ultraviolet radiation comprise emission means 5 arranged in order to emit the ultraviolet radiation.

The ultraviolet radiation has at least a wavelength comprised between 10 nm and 380 nm, preferably between 180 nm and 380 nm.

The emission means 5 are also arranged in order to emit, simultaneously with the ultraviolet radiation, at least one wavelength comprised between 380 and 1100 nm, which is advantageous for example against moulds.

These emission means 5 typically comprise at least one UV lamp.

Figure 3:
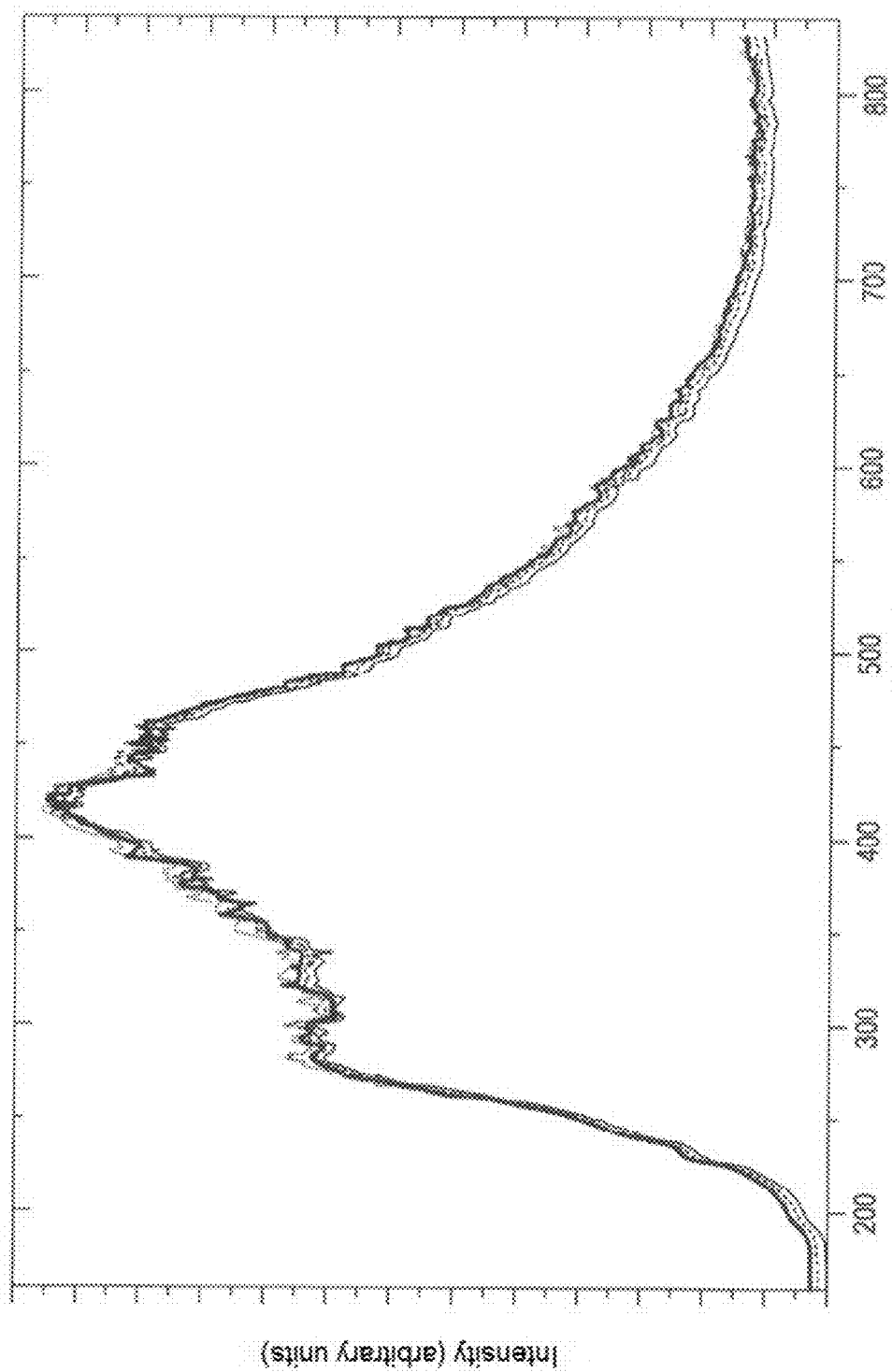
FIG. 3 shows an intensity profile of each UV lamp present in the cavity 4 as a function of the wavelength λ (in nm) emitted by this UV lamp.

Each UV lamp extends in the direction of travel 14, and comprises for example a UV lamp with Xenon gas ionization the intensity profile of which (in arbitrary units, the intensity depending on the supply voltage) is shown in FIG. 3. For each lamp, a supply voltage of 2100 V corresponds to total energy dissipated (light, heat, etc.) per pulse of 145 joules, i.e. approximately 72.5 joules of luminous energy emitted by the lamp. For each lamp, a supply voltage of 2500 V corresponds to total energy dissipated (light, heat, etc.) per pulse of 206 joules, i.e. approximately 103 joules of luminous energy emitted by the lamp.

Each UV lamp is in contact with a cooling liquid 15 (typically deionized water typically maintained between 10° C. and 35° C.), situated between the UV lamp and a quartz window 16.

The means for subjecting the tube 2 to ultraviolet radiation also comprise a cavity 4 situated on the decontamination path downstream of the heating means 8 with respect to the direction of travel 14.

The movement means 13 and the cavity 4 are arranged together with respect to one another so that:
  the first end 3 of the tube 2 is introduced inside the cavity 4 when the tube 2 arrives at the cavity 4,
  the second end 6 of the tube 2 is not located in the cavity 4 when the passing tube 2 reaches the level of the cavity 4,
  the body 7 of the tube 2 is not located in the cavity 4 when the tube 2 arrives at the cavity 4.

The cavity 4 is arranged in order to reflect the ultraviolet radiation emitted by the emission means 5 and in order to direct this ultraviolet radiation:
  onto the inner neck 3a of the tube 2
  onto the outer neck 3b of the tube 2
  inside the tube 2 via the first end 3, more precisely:
  onto the inner neck 3a already mentioned
  onto the body 7 of the tube 2 on the inner side of the tube 2
  onto the base 6 of the tube 2 on the inner side of the tube 2 so as to subject the entire interior of the tube 2, all of the outer neck 3b and all of the inner neck 3a to the ultraviolet radiation when the passing tube 2 reaches the level of the cavity 4.

The emission means 5 are arranged inside the cavity 4.

The inside of the cavity 4 is delimited by a reflective surface made from aluminium, produced in one piece from EN AW 5754.

The heating means 8, the cavity 4 and the movement means 13 linking the heating means 8 to the cavity 4 are arranged so that all the parts of the tube 2 are at a temperature:

above or equal to the temperature of transformation of the shape of the tube 2;
preferably above or equal to 85° C., preferably above or equal to 95° C., preferably above or equal to 110° C., preferably above or equal to 137° C. (for example in the case of the present embodiment for which the temperature drop of the tube 2 between the means 8 and the cavity 4 is at most 5° C.), or
preferably above or equal to 90° C., preferably above or equal to 100° C., preferably above or equal to 115° C., preferably above or equal to 142° C. (for example in an ideal case for which there is no temperature drop of the tube 2 (rounded to the nearest 1° C.) between the means 8 and the cavity 4)
when the passing tube 2 reaches the level of the cavity 4.

To this end:
  the distance between the exit of the heating means 8 and the entry of the cavity 4 is for example at maximum 100 cm, typically 30 cm or 50 cm and/or
  the movement means 13 are for example arranged in order to move the tube 2 at a speed of at least 0.1 m·s$^{-1}$, preferably at least 1 m·s$^{-1}$ between the exit of the heating means 8 and the entry of the cavity 4. The speed of the movement means 13 can be adjusted, and so can operate at a slower speed.

It is noted that the radiation emission means 5 are not arranged in order to be inserted inside the tube 2 when the passing tube 2 reaches the level of the cavity 4. This ensures that time is not lost inserting the means 5 inside the tube 2 and removing them therefrom, and allows a high speed of the method according to the invention, typically at least 25,000 tubes decontaminated per hour (typically between 5,000 and 100,000 tubes decontaminated per hour). This also makes it possible to avoid breaking the means 5 inside the tube 2 and leaving hazardous debris therein, in particular in the context of the agri-food industry.

Generally, the device 1 does not comprise any other radiation emission means arranged in order to be inserted inside the tube 2 when the passing tube 2 reaches the level of the cavity 4.

The emission means 5 are arranged in order to emit the ultraviolet radiation in the form of pulsed ultraviolet light having:
  at least one UV wavelength comprised between 180 nm and 380 nm, and
  a pulse duration less than 500 µs, typically greater than or equal to 250 µs and/or greater than or equal to 300 µs and/or
  a luminous energy per pulse, between 180 nm and 1100 nm, of at least 70 joules, preferably at least 100 joules, preferably at least 150 joules (per pulse originating from the combination of the UV lamps which emit simultaneously), at least 5% (preferably at least 10%) of which is between 180 nm and 380 nm and/or at least 50% (preferably at least 60%) between 400 nm and 700 nm, and/or
  a pulse frequency of at least 0.1 Hz, typically greater than 0.5 Hz and/or less than 20 Hz, or more generally, a pulse production controlled as a function of the rate of advance of the tubes to be decontaminated in front of the emission means 5 and/or in the cavity 4.

As shown in FIG. 3, the ultraviolet radiation is a flash of light (typically a flash of white light) comprising UV and also comprising at least one other wavelength comprised between 400 and 700 nm, i.e. "visible" light.

This radiation combines three points:

emission of UV high power, in other words the short emission time (which gives the power effect)

the "continuous" spectrum, i.e. the multiplicity of wavelengths.

The device 1 also comprises, on the decontamination path downstream of the cavity 4 with respect to the direction of travel 14, in the following order with respect to the direction of travel 14:

means 9 for modifying the shape of the tube 2, preferably by blow moulding, the tube being a preform still hot from the heating means 8 at a temperature sufficiently high for deformation thereof; for example the tube 2 is given the shape of a bottle; the means 9 can for example consist of a blow-moulding machine.

means 10 for filling the tube 2 with a liquid or food or other product through the first end 3 thereof; the means 10 can for example consist of a machine for filling with a pasty substance, gel, natural liquid, gaseous substance or of dairy or other product type.

fixing means 11 arranged for fixing a cap on the tube 2 in contact with the outer neck 3b of the tube 2; the means 11 can for example consist of a capping machine, a screw capper machine, etc.

The heating means 8 are used both for decontaminating the tube 2 and to allow the shape of the tube 2 to be modified.

This is made possible by passing the tube 2 very rapidly through the cavity 4, without losing time on inserting the emission means 5 into the tube 2 and removing them therefrom, which avoids undue cooling of the tube 2.

The device 1 does not comprise means for raising the temperature of the tube 2 along the decontamination path between the cavity 4 and the means 9 for modifying the shape of the tube 2, more generally between the cavity 4 and the means 10 for filling the tube 2, more generally between the cavity 4 and the means 11 for fixing the cap.

The device 1 comprises means 12 for subjecting the cap to ultraviolet radiation before it is fixed on the tube 2 by the fixing means 11, of the same type as those described for the means 5 and the cavity 4.

It is noted finally that the device 1 does not comprise any means for chemical decontamination of the tube. In particular, between the heating means 8 and the fixing means 11, the device 1 does not comprise any means for placing the tube 2 in contact with a liquid or product other than that used by the filling means 10 in order to fill the tube and kept within the tube 2 after fixing the cap.

For safety reasons, the UV lamps are separated from the tube 2 by quartz strips 17, 18, arranged within the cavity 4.

The embodiment of a method for microbiological contamination of the tube 2 implemented by the device 1 comprises:

initially raising the temperature of the tube 2 (i.e. at least a part of the tube; preferably all the parts of the tube or all the parts of the tube except for the neck) by the heating means 8, obtained by passing the tube 2 through the infrared lamp oven; the initial temperature increase raises all the parts of the tube to a temperature above or equal to 90° C., preferably above or equal to 100° C., preferably above or equal to 115° C., preferably above or equal to 142° C.; then subjecting the tube 2 to the ultraviolet radiation, comprising emission of the ultraviolet radiation by the emission means 5, and subjecting the inside of the tube (more precisely the inner neck 3a, the body 7 of the tube 2 on the inner side of the tube 2 and of the base 6 of the tube 2 on the inner side of the tube 2, preferably all of the inner neck 3a, all of the body 7 of the tube 2 on the inner side of the tube 2 and all of the base 6 of the tube 2 on the inner side of the tube 2), the outer neck 3b (preferably all the outer neck 3b) and the inner neck 3a (preferably all the inner neck 3a) to ultraviolet radiation, when the first end 3 is introduced inside the cavity 4.

When the tube 2 is subjected to the ultraviolet radiation, the second end 6 of the tube is not located in the cavity 4.

When the tube 2 is subjected to the ultraviolet radiation, the body 7 of the tube is not located in the cavity 4.

All the parts of the tube 2 are at a temperature:

above or equal to the temperature of transformation of the shape of the tube 2;

preferably above or equal to 85° C., preferably above or equal to 95° C., preferably above or equal to 110° C., preferably above or equal to 137° C. (for example in the case of the present embodiment for which the temperature drop of the tube 2 between the means 8 and the cavity 4 is at most 5° C.), or preferably above or equal to 90° C., preferably above or equal to 100° C., preferably above or equal to 115° C., preferably above or equal to 142° C. (for example in an ideal case for which there is no temperature drop of the tube 2 (rounded to the nearest 1° C.) between the means 8 and the cavity 4)

when the tube 2 is subjected to the ultraviolet radiation.

To this end:

the distance between the exit of the heating means 8 and the entry of the cavity 4 is for example at maximum 100 cm, and/or the movement means 13 move the tube 2 at a speed of at least 0.1 m·s$^{-1}$, preferably at least 1 m·s$^{-1}$ between the exit of the heating means 8 and the entry of the cavity 4. The preforms are preferably accelerated: for 72,000/h (20/s) they pass from 0.7 m/s to 7 m/s.

When the tube 2 is subjected to the ultraviolet radiation, the radiation emission means 5 are not inserted inside the tube 2. Generally, there is no insertion inside the tube 2 of any other radiation emission means.

The ultraviolet radiation is pulsed ultraviolet light as previously described.

The tube 2 is a tube made from plastic material, for example:

made from polyethylene terephthalate (PET)

weighing 22.5 grams with an inside diameter of the tube of 28 mm at the end 3 with a height of 90 mm.

However, it is noted that the principle of decontamination according to this embodiment is compatible with the variant in which the tube 2 can be of all types (glass, polylactic acid (PLA), etc.)

The embodiment of the method according to the invention implemented in the device 1 comprises the following steps after subjecting the tube 2 to the ultraviolet radiation, in the following order:

modifying the shape of the tube 2 by blow-moulding by the means 9, filling the tube 2 with a liquid or food or other product by the means 10, and fixing a cap on the tube 2 in contact with the outer neck 3b, by the means 11, when the liquid or product is still contained in the tube 2, but after subjecting the cap to ultraviolet radiation by the means 12.

It is noted that this embodiment of the invention allows high speed while still:
limiting the risks of debris in the tube 2,
allowing a very compact device 1,
being relatively economical and easy to maintain,
dispensing with a second increase in the temperature of the tube 2, in particular:
  between subjecting the tube 2 to the ultraviolet radiation and modifying the shape of the tube 2, and/or
  between subjecting the tube 2 to the ultraviolet radiation and filling the tube 2 (in the case where the deformation by blow-moulding does not blow hot air at a temperature above that of the tube 2), and/or
  between subjecting the tube 2 to the ultraviolet radiation and fixing the cap (in the case where the deformation by blow-moulding does not blow hot air at a temperature above that of the tube 2), and/or
dispensing with chemical decontamination that is potentially problematic in the agri-food industry; in fact this embodiment of the method according to the invention does not comprise any chemical decontamination of the tube 2. In particular, between the initial temperature increase (by the means 8) and fixing of the cap (by the means 11), the tube 2 is not in contact with any liquid or product other than that used in the filling step (by the means 10) and kept within the tube 2 after fixing of the cap.
ensuring a very efficient decontamination level inside the tube 2 (typically of at least 1 log, preferably at least 1.5 log, preferably at least 3 log, typically between 3 and 5 log), intended to be in contact with the food product, and of the outer neck 3b, intended to be in contact with the cap and/or the mouth of a user.

The level of decontamination reached is even surprising and unexpected, and a synergistic effect is noted between the heating by the means 8 and the UV decontamination by the means 5, the effect of which is greater than the sum of the effects of heating alone and UV decontamination alone.

In the present embodiment, the light decontamination by flash of white light combines two effects:
photochemical effect by the UV wavelengths
photothermal effect by the visible wavelengths; certain germs absorb visible light and are thus heated by the light flash.

The light decontamination treatment is immediate, due to the use of a pulsed technology, emitting a high-power, UV-rich white light.

Tests were carried out.

For each tube 2 tested, $5 \cdot 10^4$ CFU (colony-forming unit) of *Aspergillus brasiliensis* DSM 1988 germs were deposited and distributed:
over 16 1-μl drops on the inner neck 3a distributed over 4 vertical lines spaced apart by an angle of 90° with respect to the centre of the tube 2, and
over 50 1-μl drops on the body 7 and the base 6 on the inside of the tube 2, distributed over 4 vertical lines spaced apart by an angle of 90° with respect to the centre of the tube 2.
Decontamination measurements (each on at least five tubes 2) were carried out in order to compare the effects:
of heating alone by the means 8
of the UV decontamination alone by the means 4, 5
of synergy according to the invention between the heating by the means 8 and the UV decontamination of the inside of the tube 2 by the means 4, 5.

The table below gives the values of these decontamination measurements for some of these tests.

| Type of decontamination | Decontamination measurement (in log) |
| --- | --- |
| A) Heating alone by the heating means 8 at 115° C. (temperature of the tube 2 at the exit of the oven 8) | 2.1 |
| B) Heating alone by the heating means 8 at 142° C. (temperature of the tube 2 at the exit of the oven 8) | 2.2 |
| C) UV decontamination alone by the means 4, 5; 1 flash per UV lamp per tube 2 | 1.9 |
| D) UV decontamination alone by the means 4, 5; 2 flashes per UV lamp per tube 2 | 2.0 |
| Case of heating A) + UV decontamination D) | 4.2 |
| Case of heating B) + UV decontamination C) | 4.5 |
| Case of heating B) + UV decontamination D) | 4.4 |

The decontaminations are given in log (1 log of decontamination corresponds to a division of the number of germs by ten; 3 log of decontamination corresponds to a division by one thousand of the number of germs; 4 log of decontamination corresponds to a division of the number of germs by ten thousand, etc.) The number of germs remaining is counted according to the conventional microbiological techniques (method by inclusion in a culture medium and filtration).

Tests also show that the invention makes it possible to obtain a decontamination level greater than 4.2 log on the outer neck 3b (less critical surface).

Of course, the invention is not limited to the examples which have just been described, and numerous adjustments may be made to these examples without departing from the scope of the invention.

In particular, the description of the preceding embodiment for a tube remains valid within the framework of the invention for several tubes 2 decontaminated in series one after another and/or in parallel.

Of course, the various characteristics, forms, variants and embodiments of the invention can be combined together in various combinations inasmuch as they are not incompatible or mutually exclusive. In particular, all the variants and embodiments described above can be combined together.

Thus, in a variant of the method according to the invention, all the parts of the tube except for the neck are preferably at a temperature above or equal to 85° C. when the tube is subjected to the ultraviolet radiation, preferably above or equal to 90° C., preferably above or equal to 100° C., preferably above or equal to 115° C., preferably above or equal to 142° C.

Similarly, in a device according to the invention, the heating means, the cavity and the movement means linking the heating means to the cavity can be arranged so that all the parts of the tube except for the neck are at a temperature above or equal to 85° C. when the tube arrives at the cavity, preferably above or equal to 90° C., preferably above or equal to 100° C., preferably above or equal to 115° C., preferably above or equal to 142° C.

As the neck typically comprises parts ensuring sealing of the future bottle, this may indeed make it possible to avoid deforming it by the heat.

The invention claimed is:

1. A method for decontaminating a tube a first open end of which forms an inner neck towards the inside of the tube and an outer neck towards the outside of the tube, said method comprising:
   initially raising the temperature of the tube; then
   subjecting the tube to ultraviolet radiation, comprising emitting ultraviolet radiation by radiation emission means, and subjecting the inside of the tube, the outer neck and the inner neck to the ultraviolet radiation, when the first end is introduced inside a cavity arranged in order to reflect the ultraviolet radiation emitted by the emission means and to direct this ultraviolet radiation to the inside of the tube through the first end, onto the outer neck of the tube and onto the inner neck of the tube;
   wherein the tube comprises:
   a second end forming a base of the tube; and
   a body extending between the first end and the second end; and wherein, when the tube is subjected to the ultraviolet radiation, the second end of the tube is not located in the cavity.

2. The method according to claim 1, characterized in that, when the tube is subjected to the ultraviolet radiation, the body of the tube is not located in the cavity.

3. The method according to claim 1, characterized in that all the parts of the tube or all the parts of the tube except for the neck are at a temperature above or equal to 85° C. when the tube is subjected to the ultraviolet radiation.

4. The method according to claim 1, characterized in that, when the tube is subjected to the ultraviolet radiation, the radiation emission means are not inserted inside the tube.

5. The method according to claim 4, characterized in that it does not comprise any insertion inside the tube of any other radiation emission means.

6. The method according to claim 1, characterized in that the ultraviolet radiation comprises at least one UV wavelength comprised between 180 nm and 380 nm, and has:
   a pulse duration less than 500 µs; and/or
   a luminous energy per pulse of at least 70 joules; and/or
   a pulse frequency of at least 0.5 Hz or a pulse production controlled as a function of the rate of advance of the tubes to be decontaminated in front of the emission means and/or in the cavity.

7. The method according to claim 1, characterized in that the tube is a tube made from plastic material.

8. The method according to claim 1, characterized in that it comprises at least one of the following steps after subjecting the tube to the ultraviolet radiation, in the following order:
   modifying the tube shape; and/or
   filling the tube; and/or
   fixing a cap on the tube in contact with the outer neck.

9. The method according to claim 8, characterized in that it does not comprise any increase in the temperature of the tube:
   between subjecting the tube to the ultraviolet radiation and modifying the shape of the tube; and/or
   between subjecting the tube to the ultraviolet radiation and filling the tube; and/or
   between subjecting the tube to the ultraviolet radiation and fixing the cap.

10. The method according to claim 8, characterized in that it comprises subjecting the cap to ultraviolet radiation before it is fixed on the tube.

11. The method according to claim 1, characterized in that it does not comprise any chemical decontamination of the tube.

12. The method according to claim 1, characterized in that the initial temperature increase is obtained by passing the tube through an oven and/or by subjecting the tube to an infrared lamp.

13. The method according to claim 1, characterized in that the initial temperature increase raises all the parts of the tube to a temperature above or equal to 90° C.

14. A decontamination device of a tube comprising:
   means for moving, along a decontamination path in a direction of travel, a tube a first open end of which forms an inner neck towards the inside of the tube and an outer neck towards the outside of the tube;
   initial heating means, arranged in order to raise the temperature of the tube on the decontamination path;
   means for subjecting the tube to ultraviolet radiation, comprising emission means arranged in order to emit the ultraviolet radiation, and a cavity situated on the decontamination path downstream of the heating means with respect to the direction of travel, the movement means and the cavity being arranged together so that the first end is introduced inside the cavity when the tube arrives at the cavity; and
   the cavity being arranged in order to reflect the ultraviolet radiation emitted by the emission means and to direct this ultraviolet radiation to the inside of the tube through the first end, onto the outer neck of the tube and onto the inner neck of the tube so as to subject the inside of the tube, the outer neck and the inner neck to the ultraviolet radiation when the tube arrives at the cavity;
   the tube comprising:
   a second end forming a base of the tube; and
   a body extending between the first end and the second end; wherein the second end of tube is not within the cavity when the tube is subjected to the ultraviolet radiation.

15. A decontamination device of a tube comprising:
   a conveyor configured for moving, along a decontamination path in a direction of travel, a tube a first open end of which forms an inner neck towards the inside of the tube and an outer neck towards the outside of the tube;
   an initial heater, arranged in order to raise the temperature of the tube on the decontamination path;
   at least one ultraviolet lamp for subjecting the tube to ultraviolet radiation, and a cavity situated on the decontamination path downstream of the initial heater with respect to the direction of travel, the conveyor and the cavity being arranged together so that the first end is introduced inside the cavity when the tube arrives at the cavity; and
   the cavity being arranged in order to reflect the ultraviolet radiation emitted by the at least one ultraviolet lamp and to direct this ultraviolet radiation to the inside of the tube through the first end, onto the outer neck of the tube and onto the inner neck of the tube so as to subject the inside of the tube, the outer neck and the inner neck to the ultraviolet radiation when the tube arrives at the cavity;
   the tube comprising:
   a second end forming a base of the tube; and
   a body extending between the first end and the second end; wherein the second end of the tube is not within the cavity when the tube is subjected to the ultraviolet radiation.

* * * * *